United States Patent

Momose et al.

[11] Patent Number: 6,110,948
[45] Date of Patent: Aug. 29, 2000

[54] ANTICACHECTIC COMPOSITION

[75] Inventors: Yu Momose, Takarazuka; Etsuya Matsutani, Suita; Takashi Sohda, Takatsuki, all of Japan

[73] Assignee: Takeda Chemical Industries, Ltd., Osaka, Japan

[21] Appl. No.: 09/155,593

[22] PCT Filed: Apr. 3, 1997

[86] PCT No.: PCT/JP97/01148

§ 371 Date: Sep. 30, 1998

§ 102(e) Date: Sep. 30, 1998

[87] PCT Pub. No.: WO97/37656

PCT Pub. Date: Oct. 16, 1997

[30] Foreign Application Priority Data

Apr. 4, 1996 [JP] Japan .................................. 8-082845
Feb. 12, 1997 [JP] Japan .................................. 9-027957

[51] Int. Cl.[7] .......................... A61K 31/44; A61K 31/42; A61K 31/425; A61K 31/40

[52] U.S. Cl. .......................... 514/343; 514/376; 514/369; 514/425

[58] Field of Search .................. 514/376, 369, 514/343, 425

[56] References Cited

U.S. PATENT DOCUMENTS

| | | | |
|---|---|---|---|
| 4,775,687 | 10/1988 | Meguro et al. | 514/369 |
| 5,478,852 | 12/1995 | Olefsky et al. | 514/369 |
| 5,665,748 | 9/1997 | Sohda et al. | 514/365 |

FOREIGN PATENT DOCUMENTS

| | | |
|---|---|---|
| 0 008 203 A1 | 2/1980 | European Pat. Off. . |
| 0 612 743 A1 | 8/1994 | European Pat. Off. . |
| 0 710 659 A1 | 5/1996 | European Pat. Off. . |
| 7-285864 | 10/1995 | Japan . |
| 94/25026 | 11/1994 | WIPO . |
| 96/04909 | 2/1996 | WIPO . |

*Primary Examiner*—Jerome D. Goldberg
*Attorney, Agent, or Firm*—Wenderoth, Lind & Ponack, LLP.

[57] ABSTRACT

A medicinal composition for the prophylaxis and treatment of cachexia which comprises a compound of the formula:

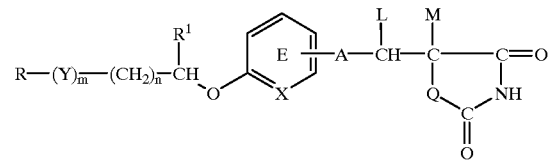

wherein R represents a hydrocarbon group that may be substituted or a heterocyclic group that may be substituted; Y represents a group of the formula —CO—, —CH(OH)—, or —NR$^3$— (R$^3$ represents an alkyl group that may be substituted); m is 0 or 1; n is 0, 1 or 2; X represents CH or N; A represents a bond or a bivalent aliphatic hydrocarbon group having 1 to 7 carbon atoms; Q represents oxygen or sulfur; R$^1$ represents hydrogen or an alkyl group; ring E may have further 1 to 4 substituents, which may form a ring in combination with R$^1$; L and M respectively represent hydrogen or may be combined with each other to form a bond, provided that when m and n are 0, X represents CH, A represents a bond, Q represents sulfur, R$^1$, L and M respectively represent hydrogen, and ring E does not have further substituents, R does not represent dihydrobenzopyranyl; or a salt thereof.

11 Claims, No Drawings

ANTICACHECTIC COMPOSITION

TECHNICAL FIELD

The present invention relates to a medicinal composition for the prophylaxis and treatment of cachexia which develops in chronic diseases such as malignant tumor, tuberculosis, diabetes, blood dyscrasia, endocrine disease, infectious disease, or acquired immunodeficiency syndrome.

BACKGROUND ART

Cachexia is a systemic syndrome with progressive loss of body weight, anemia, edema, and anorexia as cardinal symptoms which develops in chronic diseases such as malignant tumor, tuberculosis, diabetes, blood dyscrasia, endocrine disease, infectious disease, and acquired immunodeficiency syndrome [e.g. Kern et al., Cancer Cachexia, J. Parenteral and Enteral Nutrition, 12, 286–298 (1988) and American Journal of Medicine, 85, 289–291 (1988)].

In cachexia, therapeutic nutrition and endocrine therapy are generally administered but a satisfactory anticachectic modality remains to be established. Particularly where cachexia is caused by a malignant tumor, the available anticancer chemotherapy cannot be administered when cachexia is progressing, with the result that the treatment encounters a serious setback. Moreover, any therapeutic nutrition for relief of cachectic symptoms may rather exacerbate the malignant tumor and detract from the life expectancy of the patient. While cachexia is frequently caused by the malignant tumors, administration of an antitumor agent in such settings may result in control of the tumors but generally side effects of the drug develop in superimposition, the net result being no improvement in cachexia [Nelson et al., Journal of Clinical Oncology, 12, 213–225 (1994)].

In the above state of the art, there is a standing need for an anticachectic composition that should ameliorate or inhibit progression of cachectic symptoms such as loss of body weight.

DISCLOSURE OF INVENTION

The present invention relates to a medicinal composition for the prophylaxis and treatment of cachexia which comprises a compound of the formula:

$$R-(Y)_{\overline{m}}-(CH_2)_{\overline{n}}-CH(R^1)-\underset{O}{\underbrace{\phantom{X}}}\underset{X}{\underbrace{E}}-A-CH(L)-C(M)(Q-C(=O)-NH)-C=O \quad (I)$$

wherein R represents a hydrocarbon group that may be substituted or a heterocyclic group that may be substituted; Y represents a group of the formula —CO—, —CH(OH)—, or —NR³— (R³ represents an alkyl group that may be substituted); m is 0 or 1; n is 0, 1 or 2; X represents CH or N; A represents a bord or a bivalent aliphatic hydrocarbon group having 1 to 7 carbon atoms; Q represents oxygen or sulfur; R¹ represents hydrogen or an alkyl group; ring E may have further 1 to 4 substituents, which may form a ring in combination with R¹; L and M respectively represent hydrogen or may be combined with each other to form a bond; provided that when m and n are 0, X represents CH, A represents a bond, Q represents sulfur, R¹, L and M respectively represent hydrogen, and ring E does not have further substituents, R does not represent dihydrobenzopyranyl; or a salt thereof (hereinafter referred to simply as Compound (I)).

Referring to the hydrocarbon group that may be substituted for R, the hydrocarbon group includes aliphatic, alicyclic, alicyclic-aliphatic, aromatic-aliphatic, and aromatic hydrocarbon groups. The preferred number of carbon atoms constituting such hydrocarbon groups is 1 to 14.

The aliphatic hydrocarbon group is preferably a $C_{1-8}$ aliphatic hydrocarbon group. The aliphatic hydrocarbon group includes saturated $C_{1-8}$ aliphatic hydrocarbon groups (e.g. alkyl groups) such as methyl, ethyl, propyl, isopropyl, butyl, isobutyl, sec-butyl, t-butyl, pentyl, isopentyl, neopentyl, t-pentyl, hexyl, isohexyl, heptyl, and octyl; and unsaturated $C_{2-8}$ aliphatic hydrocarbon groups (e.g. alkenyl, alkadienyl, alkynyl, and alkadiynyl groups) such as ethenyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl, and 1-octynyl.

The alicyclic hydrocarbon group is preferably a $C_{3-7}$ alicyclic hydrocarbon group. The alicyclic hydrocarbon group includes saturated $C_{3-7}$ alicyclic hydrocarbon groups (e.g. cycloalkyl groups) such as cyclopropyl, cyclobutyl, cyclopentyl, cyclohexyl, cycloheptyl, etc. and unsaturated $C_{5-7}$ alicyclic hydrocarbon groups (e.g. cycloalkenyl and cycloalkadienyl groups) such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl, and 2,4-cycloheptadienyl.

The alicyclic-aliphatic hydrocarbon group is a group consisting of the above-described alicyclic hydrocarbon group and aliphatic hydrocarbon group (e.g. cycloalkyl-alkyl and cycloalkenyl-alkyl groups) and is preferably a $C_{4-9}$ alicyclic-aliphatic hydrocarbon group. Specifically, the alicyclic-aliphatic hydrocarbon group includes cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl, cycloheptylethyl, etc.

The aromatic-aliphatic hydrocarbon group is preferably a $C_{7-13}$ aromatic-aliphatic hydrocarbon group (e.g. aralkyl and arylalkenyl groups). The aromatic-aliphatic hydrocarbon group includes $C_{7-9}$ phenylalkyl such as benzyl, phenethyl, 1-phenylethyl, 3-phenylpropyl, 2-phenylpropyl and 1-phenylpropyl; $C_{11-13}$ naphthylalkyl such as α-naphthylmethyl, α-naphthylethyl, β-naphthylmethyl, and β-naphthylethyl; $C_{8-10}$ phenylalkenyl such as styryl and 4-phenyl-1,3-butadienyl; and $C_{12-13}$ naphthylalkenyl such as 2-(2-naphthyl)vinyl.

The aromatic hydrocarbon group is preferably a $C_{6-14}$ aromatic hydrocarbon group (e.g. aryl groups). The aromatic hydrocarbon group includes phenyl and naphthyl (α-naphthyl, β-naphthyl).

Referring to the formula (I), the heterocyclic group in a heterocyclic group that may be substituted for R is a 5- to 7-membered monocyclic heterocyclic group containing 1 to 4 hetero-atoms selected from oxygen, sulfur, and nitrogen in addition to carbon as ring members or a condensed heterocyclic ring group. The condensed heterocyclic ring may for example be one consisting of such a 5- to 7-membered monocyclic heterocyclic group and a 6-membered ring containing 1 or 2 nitrogen atoms, a benzene ring, or a 5-membered ring containing one sulfur atom.

Specifically the heterocyclic group includes 2-pyridyl, 3-pyridyl, 4-pyridyl, 2-pyrimidinyl, 4-pyrimidinyl, 5-pyrimidinyl, 6-pyrimidinyl, 3-pyridazinyl, 4-pyridazinyl, 2-pyrazinyl, 2-pyrrolyl, 3-pyrrolyl, 2-imidazolyl, 4-imidazolyl, 5-imidazolyl, 3-pyrazolyl, 4-pyrazolyl, isothiazolyl, isoxazolyl, 2- thiazolyl, 4-thiazolyl, 5-thiazolyl, 2-oxazolyl, 4-oxazolyl, 5-oxazolyl, 1,2,4-oxadiazol-5-yl, 1,2,4-triazol-3-yl, 1,2,3-triazol-4-yl, tetrazol-5-yl, benzimidazol-2-yl, indol-3-yl, 1H-indazol-3-yl, 1H-pyrrolo[2,3-b]pyrazin-2-yl, 1H-pyrrolo[2,3-b]pyridin-6-yl, 1H-imidazo[4,5-b]pyridin-2-yl, 1H-imidazo[4,5-c]pyridin-2-yl, 1H-imidazo[4,5-b]pyrazin-2-yl, and benzopyranyl. The preferred heterocyclic group is pyridyl, oxazolyl, or thiazolyl.

Referring to the formula (I), the hydrocarbon group and heterocyclic group for R may respectively have 1 to 5, preferably 1 to 3 substituents at substitutable positions. Such substituents include for example aliphatic hydrocarbon groups, alicyclic hydrocarbon groups, aryl groups, aromatic heterocyclic groups, nonaromatic heterocyclic groups, halogen, nitro, amino group that may be substituted, acyl groups that may be substituted, hydroxy group that may be substituted, thiol that may be substituted, and carboxyl group that may be esterified.

The aliphatic hydrocarbon group includes straight-chain or branched aliphatic hydrocarbon groups having 1 to 15 carbon atoms, such as alkyl, alkenyl, and alkynyl groups.

The preferred alkyl group is a $C_{1-10}$ alkyl group, such as methyl, ethyl, propyl, isopropyl, butyl, isobutyl, sec-butyl, t-butyl, pentyl, isopentyl, neo-pentyl, t-pentyl, 1-ethylpropyl, hexyl, isohexyl, 1,1-dimethylbutyl, 2,2-dimethylbutyl, 3,3-dimethylbutyl, 2-ethylbutyl, hexyl, pentyl, octyl, nonyl, and decyl.

The preferred alkenyl group is a $C_{2-10}$ alkenyl group, such as vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, and 5-hexenyl.

The preferred alkynyl group is a $C_{2-10}$ alkynyl group, such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, and 5-hexynyl.

The alicyclic hydrocarbon group includes saturated and unsaturated alicyclic hydrocarbon groups having 3 to 12 carbon atoms, such as cycloalkyl, cycloalkenyl, and cycloalkadienyl groups.

The preferred cycloalkyl group is a $C_{3-10}$ cycloalkyl group, such as cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, and bicyclo[4.3.1]decyl.

The preferred cycloalkenyl group is a $C_{3-10}$ cycloalkenyl group, such as 2-cyclopenten-1-yl, 3-cyclopenten-1-yl, 2-cyclohexen-1-yl, 3-cyclohexen-1-yl.

The preferred cycloalkadienyl group is a $C_{4-10}$ cycloalkadienyl group, such as 2,4-cyclopentadien-1-yl, 2,4-cyclohexadien-1-yl, 2,5-cyclohexadien-1-yl.

The term "aryl group" means a monocyclic or condensed polycyclic aromatic hydrocarbon group. As preferred examples, $C_{6-14}$ aryl groups such as phenyl, naphthyl, anthryl, phenanthryl, acenaphthylenyl can be mentioned. Particularly preferred are phenyl, 1-naphthyl, and 2-naphthyl.

The preferred aromatic heterocyclic group includes 5- to 7-membered monocyclic aromatic heterocyclic groups containing 1 to 4 hetero-atoms selected from oxygen, sulfur, and nitrogen in addition to carbon as ring members, such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, and triazinyl; and dicyclic or tricyclic condensed aromatic heterocyclic groups containing 1 to 5 hetero-atoms selected from oxygen, sulfur, and nitrogen in addition to carbon as ring members, such as benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, and 1,2,4-triazolo[4,3-b]pyridazinyl.

The preferred nonaromatic heterocyclic group includes oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, pyrrolidino, piperidino, and morpholino.

The halogen includes fluorine, chlorine, bromide, and iodine, and is preferably fluorine or chlorine.

The amino group that may be substituted includes amino (—NH$_2$) that may be mono- or di-substituted by, for example, $C_{1-10}$ alkyl groups, $C_{3-10}$ cycloalkyl groups, $C_{2-10}$ alkenyl groups, $C_{3-10}$ cycloalkenyl groups, $C_{1-13}$ acyl groups (e.g. $C_{2-10}$ alkanoyl groups, $C_{7-13}$ arylcarbonyl groups), or $C_{6-12}$ aromatic groups. As examples of the substituted amino group, there can be mentioned methylamino, dimethylamino, ethylamino, diethylamino, dibutylamino, diallylamino, cyclohexylamino, acetylamino, propionylamino, benzoylamino, phenylamino, and N-methyl-N-phenylamino.

The acyl group in the acyl groups that may be substituted includes $C_{1-13}$ acyl groups. For example, formyl and groups formed between carbonyl and $C_{1-10}$ alkyl, $C_{3-10}$ cycloalkyl, $C_{2-10}$ alkenyl, $C_{3-10}$ cycloalkenyl, $C_{6-12}$ aryl, or aromatic heterocyclic groups (e.g. thienyl, furyl, pyridyl). The preferred acyl group includes acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl, nicotinoyl. The substitutent in the substituted acyl groups includes $C_{1-3}$ alkyl, $C_{1-3}$ alkoxy groups, halogen (e.g. chlorine, fluorine, bromine, etc.), nitro, hydroxy, and amino.

Referring to the hydroxy group that may be substituted, the substituted hydroxy includes alkoxy, alkenyloxy, aralkyloxy, acyloxy, and aryloxy groups.

The preferred alkoxy group includes $C_{1-10}$ alkoxy groups, such as methoxy, ethoxy, propoxy, isopropoxy, butoxy, isobutoxy, sec-butoxy, t-butoxy, pentyloxy, isopentyloxy, neopentyloxy, hexyloxy, heptyloxy, nonyloxy, cyclobutoxy, cyclopentyloxy, and cyclohexyloxy.

The preferred alkenyloxy group includes $C_{2-10}$ alkenyloxy groups, such as allyloxy, crotyloxy, 2-pentenyloxy, 3-hexenyloxy, 2-cyclopentenylmethoxy, and 2-cyclohexenylmethoxy.

The preferred aralkyloxy group includes $C_{7-10}$ aralkyloxy groups, such as phenyl-$C_{1-4}$ alkyloxy (e.g. benzyloxy, phenethyloxy, etc.).

The preferred acyloxy group includes $C_{2-13}$ acyloxy groups, more preferably $C_{2-4}$ alkanoyloxy (e.g. acetyloxy, propionyloxy, butyryloxy, isobutyryloxy, etc.).

The preferred aryloxy group includes $C_{6-14}$ aryloxy groups, such as phenoxy, and naphthyloxy. This aryloxy group may have 1 or 2 substituents such as halogen (e.g. chlorine, fluorine, bromine, etc.). The substituted aryloxy group includes 4-chlorophenoxy.

Referring to the thiol group that may be substituted, the substituted thiol group includes alkylthio, cycloalkylthio, aralkylthio, and acylthio groups.

The preferred alkylthio group includes $C_{1-10}$ alkylthio groups, such as methylthio, ethylthio, propylthios, isopropylthio, butylthio, isobutylthio, sec-butylthio, t-butylthio, pentylthio, isopentylthio, neopentylthio, hexylthio, heptylthio, and nonylthio. The preferred cycloalkylthio group includes $C_{3-10}$ cycloalkylthio groups such as cyclobutylthio, cyclopentylthio, and cyclohexylthio.

The preferred aralkylthio group includes $C_{7-10}$ aralkylthio groups, such as phenyl-$C_{1-4}$ alkylthio (e.g. benzylthio, phenethylthio, etc.).

The acylthio group is preferably a $C_{2-13}$ acylthio group, more preferably a $C_{2-4}$ alkanoylthio group (e.g. acetylthio, propionylthio, butyrylthio, isobutyrylthio, etc.).

The carboxyl group that may be esterified includes alkoxycarbonyl, aralkyloxycarbonyl, and aryloxycarbonyl groups.

The preferred alkoxycarbonyl group includes $C_{2-5}$ alkoxycarbonyl groups, such as methoxycarbonyl, ethoxycarbonyl, propoxycarbonyl, and butoxycarbonyl.

The preferred aralkyloxycarbonyl group includes $C_{8-10}$ aralkyloxycarbonyl groups, such as benzyloxycarbonyl.

The preferred aryloxycarbonyl group includes $C_{7-15}$ aryloxycarbonyl groups, such as phenoxycarbonyl, and p-tolyloxycarbonyl.

The preferred substituent on the hydrocarbon or heterocyclic group for R includes $C_{1-10}$ alkyl groups, aromatic heterocyclic groups, and $C_{6-14}$ aryl groups. Particularly preferred is $C_{1-3}$ alkyl, furyl, thienyl, phenyl, or naphthyl.

Referring to the formula (I), when the substituent on the hydrocarbon or heterocyclic group for R is an alicyclic hydrocarbon group, an aryl group, an aromatic heterocyclic group, or a nonaromatic heterocyclic group, this substituent may be further substituted by one or more, preferably 1 to 3 suitable substituents. As such substituents, there can be mentioned $C_{1-6}$ alkyl groups, $C_{2-6}$ alkenyl groups, $C_{2-6}$ alkynyl groups, $C_{3-7}$ cycloalkyl groups, C6-14 aryl groups (e.g. phenyl, naphthyl, etc.), aromatic heterocyclic groups (e.g. thienyl, furyl, pyridyl, oxazolyl, thiaizolyl, etc.), non-aromatic heterocyclic groups (e.g. tetrahydrofuryl, morpholino, thiomorpholino, piperidino, pyrrolidino, piperazino, etc.), $C_{7-9}$ aralkyl groups, amino, N-mono($C_{1-4}$)alkylamino groups, N,N-di($C_{1-4}$)alkylamino groups, $C_{2-8}$ acylamino groups (e.g. acetylamino, propionylamino, benzoylamino, etc.), amidino, $C_{2-8}$ acyl groups (e.g. $C_{2-8}$ alkanoyl groups, etc.), carbamoyl, N-mono($C_{1-4}$)alkylcarbamoyl groups, N,N-di($C_{1-4}$)alkylcarbamoyl groups, sulfamoyl, N-mono($C_{1-4}$)alkylsulfamoyl groups, N,N-di($C_{1-4}$)alkylsulfamoyl groups, carboxyl, $C_{2-8}$ alkoxycarbonyl groups, hydroxy, $C_{1-4}$ alkoxy groups, $C_{2-5}$ alkenyloxy groups, $C_{3-7}$ cycloalkyloxy groups, $C_{7-9}$ aralkyloxy groups, $C_{6-14}$ aryloxy groups (e.g. phenyloxy, naphthyloxy, etc.), mercapto, $C_{1-4}$ alkylthio groups, $C_{7-9}$ aralkylthio groups, $C_{6-14}$ arylthio groups (e.g. phenylthio, naphthylthio, etc.), sulfo, cyano, azido, nitro, nitroso, and halogen (e.g. fluorine, chlorine, bromine, iodine).

In the formula (I), R is preferably a heterocyclic group that may be substituted. More preferably, R is pyridyl, oxazolyl, or thiazolyl group, which may have 1 to 3 substituents selected from $C_{1-3}$ alkyl, furyl, thienyl, phenyl, and naphthyl.

Referring to the formula (I), Y represents —CO—, —CH(OH)—, or —NR$^3$—. Y is preferably —CH(OH)— or —NR$^3$— and more preferably —CH(OH)—. Referring to an alkyl group that may be substituted for R$^3$, the alkyl group includes $C_{1-4}$ alkyl groups, such as methyl, ethyl, propyl, isopropyl, butyl, isobutyl, sec-butyl, and t-butyl. The substituent includes halogen (e.g. fluorine, chlorine, bromine, iodine), $C_{1-4}$ alkoxy groups (e.g. methoxy, ethoxy, propoxy, butoxy, isobutoxy, sec-butoxy, t-butoxy), hydroxy, nitro, and $C_{1-4}$ acyl groups (e.g formyl, acetyl, propionyl, etc.).

The symbol n represents 0, 1 or 2 and is preferably 0 or 1.

The symbol X represents CH or N and is preferably CH.

Referring to the formula (I), A represents a bond or a bivalent aliphatic hydrocarbon group having 1 to 7 carbon atoms. This aliphatic hydrocarbon group may be straight-chain or branched and may further be saturated or unsaturated. Thus, for example, —CH$_2$—, —CH(CH$_3$)—, —(CH$_2$)$_2$—, —CH(C$_2$H$_5$)—, —(CH$_2$)$_3$—, —(CH$_2$)$_4$—, —(CH$_2$)$_5$—, —(CH$_2$)$_6$—, —(CH$_2$)$_7$—, etc. can be mentioned for the saturated bivalent aliphatic hydrocarbon group, while —CH=CH—, —C(CH$_3$)=CH—, —CH=CH—CH$_2$—, —C(C$_2$H$_5$)=CH—, —CH$_2$—CH=CH—CH$_2$—, —CH$_2$—CH$_2$—CH=CH—CH$_2$—, —CH=CH—CH=CH—CH$_2$—, —CH=CH—CH=CH—CH=CH—CH$_2$—, etc. can be mentioned for the unsaturated bivalent aliphatic hydrocarbon group. The symbol A preferably represents a bond or a bivalent aliphatic hydrocarbon group having 1 to 4 carbon atoms, which is preferably a saturated group. More preferably, A represents a bond, —CH$_2$—or —(CH$_2$)$_2$—. Still more preferably, A represents a bond or —(CH$_2$)$_2$—.

The alkyl group for R$^1$ includes $C_{1-4}$ alkyl groups such as methyl, ethyl, propyl, isopropyl, butyl, isobutyl, sec-butyl, and t-butyl. Preferably, R$^1$ represents hydrogen.

Referring to the formula (I), the partial structural formula:

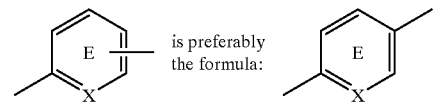

wherein each symbols has the same meanings as defined above.

Furthermore, ring E may optionally have 1 to 4 substituents at substitutable positions. Such substituents include an alkyl group, a hydroxy group that may be substituted, halogen, an acyl group that may be substituted, nitro, and an amino group that may be substituted. These substituents may be the same as the substituents mentioned for the hydrocarbon or heterocyclic group for R.

Ring E, the partial structural formula:

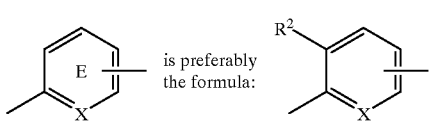 is preferably the formula: 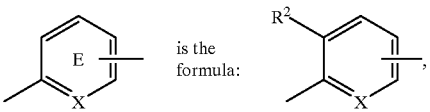

wherein $R^2$ represents hydrogen, an alkyl group, a hydroxy group that may be substituted, halogen, an acyl group that may be substituted, nitro, or an amino group that may be substituted.

The alkyl group, hydroxy group that may be substituted, halogen, acyl group that may be substituted, and amino group that may be substituted, for $R^2$, may each be the same as that mentioned for the hydrocarbon or heterocyclic group for R. Preferably, $R^2$ is hydrogen, hydroxy group that may be substituted, or halogen. More preferably, $R^2$ is hydrogen or hydroxy group that may be substituted. Particularly preferred is hydrogen or a $C_{1-4}$ alkoxy group.

L and M respectively represent hydrogen or may be combined with each other to form a bond, and preferably they are hydrogen.

Referring to the formula (I), the compound in which L and M are combined with each other to form a bond:

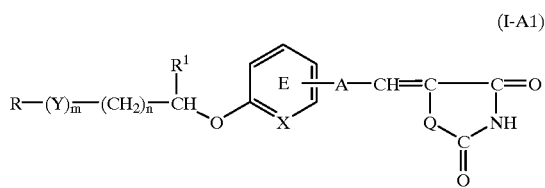

(I-A1)

wherein each symbols has the same meanings as defined above, may exist as (E)- and (Z)-isomers, owing to the double bond at 5-position of the azolidinedione ring.

The compound in which L and M respectively represent hydrogen:

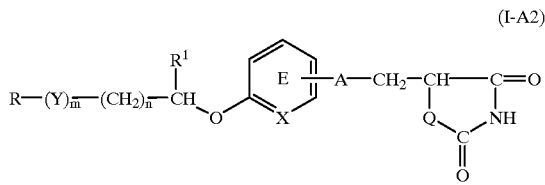

(I-A2)

wherein each symbols has the meanings as defined above, may exist as optical isomers, i.e. (R)- and (S)-forms, with respect to the asymmetric carbon at 5-position of the azolidinedione ring. This compound includes those optically active compounds, i.e. (R)- and (S)-forms, as well as the racemic form.

Referring to the formula (I) of the present invention, when m and n are 0; X represents CH; A represents a bond; Q represents sulfur; $R^1$, L, and M respectively represent hydrogen; and ring E does not have further substituents, R is not dihydrobenzopyranyl.

The preferred compound of the formula (I) is the compound in which R represents pyridyl, oxazolyl, or thiazolyl group, optionally having 1 to 3 substituents selected from the group consisting of $C_{1-3}$ alkyl, furyl, thienyl, phenyl, and naphthyl; Y represents —CH(OH)—; n is 0 or 1; X represents CH; A represents a bond or —(CH$_2$)$_2$—; $R^1$ represents hydrogen; ring E, namely the partial structural formula:

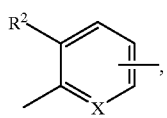 is the formula:

$R^2$ is hydrogen or a $C_{1-4}$ alkoxy group; and L and M respectively represent hydrogen.

As preferred species of the compound of the formula (I), the following compounds (1) to (7) are mentioned.

(1) 5-[4-[2-(5-ethyl-2-pyridyl)ethoxy]benzyl]-2,4-thiazolidinedione,
(2) 5-[4-[2-hydroxy-2-(5-methyl-2-phenyl-4-oxazolyl)ethoxy]benzyl]-2,4-thiazolidinedione,
(3) (R)-(+)-5-[3-[4-[2-(2-furyl)-5-methyl-4-oxazolylmethoxy]-3-methoxyphenyl]propyl]-2,4-oxazolidinedione,
(4) (S)-(−)-5-[3-[4-[2-(2-furyl)-5-methyl-4-oxazolylmethoxy]-3-methoxyphenyl]propyl]-2,4-oxazolidinedione,
(5) 5-[3-[3-fluoro-4-(5-methyl-2-phenyl-4-oxazolylmethoxy)phenyl]propyl]-2,4-oxazolidinedione,
(6) 5-[5-[3-methoxy-4-(5-methyl-2-phenyl-4-oxazolylmethoxy)phenyl]pentyl]-2,4-oxazolidinedione,
(7) 5-[3-[3,5-dimethoxy-4-[2-[(E)-styryl]-4-oxazolylmethoxy]phenyl]propyl]-2,4-oxazolidinedione (hereafter, these compounds are sometimes simply referred to as compound (1), compound (2), and the like).

Among the above compounds, compounds (1) to (3), (5), and (6) are preferred, and compounds (1) to (3) are particularly preferred.

The salt of compound (I) of the present invention is preferably a pharmacologically acceptable salt, which includes salts with inorganic bases, salts with organic bases, salts with inorganic acids, salts with organic acids, and salts with basic or acidic amino acids.

The preferred salt with an inorganic base includes alkali metal salts such as sodium salt, potassium salt, etc.; alkaline earth metal salts such as calcium salt, magnesium salt, etc.; aluminum salt, and ammonium salts.

The preferred salt with an organic base includes salts with trimethylamine, triethylamine, pyridine, picoline, ethanolamine, diethanolamine, triethanolamine, dicyclohexylamine, N,N'-dibenzylethylenediamine, etc.

The preferred salt with an inorganic acid includes salts with hydrochloric acid, hydrobromic acid, nitric acid, sulfuric acid, phosphoric acid, etc.

The preferred salt with an organic acid includes salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.

The preferred salt with a basic amino acid includes salts with arginine, lysine, ornithine, etc. The preferred salt with an acidic amino acid includes salts with aspartic acid, glutamic acid, etc.

The most preferred of all the above-mentioned salts is sodium salt or potassium salt.

Compound (I) or a salt thereof of the present invention can be produced in accordance with methods described in JP-A S55(1980)-22636 (EP-A-8203), JP-A S60(1985)-208980 (EP-A-155845), JP-A S61(1986)-286376 (EP-A-208420), JP-A S61(1986)-085372 (EP-A-177353), JP-A S61(1986)-267580 (EP-A-193256), JP-A H5(1993)-86057 (WO-A-9218501), JP-A H7(1995)-82269 (EP-A-605228), JP-A H7(1995)-101945 (EP-A-612743), EP-A-643050, EP-A-710659 (JP Application H7(1995)-284106), etc, or methods analogous thereto.

Compound (I) or a salt thereof of the present invention (hereinafter referred to as compound of the present invention) have anticachectic activity, that is the activity to relieve the systemic syndrome featuring progressive loss of body weight (inclusive of weight loss due to lipolysis and weight loss due to myolysis), anemia, edema, and anorexia in chronic diseases such as malignant tumor, tuberculosis, diabetes, blood dyscrasia, endocrine disease, infectious disease, and acquired immunodeficiency syndrome. In addition, the toxic potential of the compound of the present invention is low.

The composition for prophylaxis and treatment of the present invention can be used as an agent for prophylaxis and treatment of cachexia or an agent for treatment of malnutrition in mammals (e.g man, mouse, rat, rabbit, dog, cat, bovine, equine, swine, monkey, etc.).

The cachexia is, for example, cancer cachexia, tuberculous cachexia, diabetic cachexia, hemodyscrasia-related cachexia, endocrine disease-associated cachexia, infectious disease-associated cachexia, or acquired immunodeficiency syndrome-associated cachexia.

The composition for prophylaxis and treatment of the present invention can be used preferably in cachexia associated with malignant tumor, especially a carcinoma.

The composition for prophylaxis and treatment of the present invention includes the compound of the invention as such. Usually, the composition is provided in a pharmaceutical dosage form by formulating the compound of the invention with per se known pharmaceutically acceptable carriers.

As the pharmaceutically acceptable carrier a variety of organic and inorganic carriers in common use as raw materials for pharmaceutical preparations are employed. Thus, the carrier includes the excipient, lubricant, binder, and disintegrator for a solid dosage form; and the solvent, solubilizer, suspending agent, isotonizing agent, buffering agent and local analgesic for a liquid dosage form. Where necessary, pharmaceutical additives such as the preservative, antioxidant, coloring agent, sweetener, etc. can also be used.

The preferred excipient includes lactose, sucrose, D-mannitol, starch, crystalline cellulose, light silicic anhydride, etc.

The preferred lubricant includes magnesium stearate, calcium stearate, talc, colloidal silica, etc.

The preferred binder includes crystalline cellulose, sucrose, D-mannitol, trehalose, dextrin, hydroxypropylcellulose, hydroxypropylmethylcellulose, polyvinylpyrrolidone, etc.

The preferred disintegrator includes starch, carboxymethylcellulose, carboxymethylcellulose calcium, croscarmellose sodium, carboxymethylstarch sodium, etc.

The preferred solvent includes water for injection, alcohol, propylene glycol, macrogol, sesame oil, corn oil, tricaprylin, etc.

The preferred solubilizer includes polyethylene glycol, propylene glycol, D-mannitol, trehalose, benzyl benzoate, ethanol, trisaminomethane, cholesterol, triethanolamine, sodium carbonate, sodium citrate, etc.

The preferred suspending agent includes surfactants such as stearyltriethanolamine, sodium lauryl sulfate, laurylaminopropionic acid, lecithin, benzalkonium chloride, benzethonium chloride, glyceryl monostearate, etc. and hydrophilic polymers such as polyvinyl alcohol, polyvinylpyrrolidone, carboxymethylcellulose sodium, methylcellulose, hydroxymethylcellulose, hydroxyethylcellulose, and hydroxypropylcellulose.

The preferred isotonizing agent includes sodium chloride, glycerin, D-mannitol, etc.

The preferred buffering agent includes buffer solutions such as phosphate, acetate, carbonate, citrate.

The preferred local anesthetic includes benzyl alcohol.

The preferred antiseptic includes p-hydroxybenzoic esters, chlorobutanol, benzyl alcohol, phenethyl alcohol, dehydroacetic acid, sorbic acid, etc.

The preferred antioxidant includes salts of sulfurous acid, ascorbic acid, etc.

The above medicinal composition can be manufactured by the established pharmaceutical procedures, for example the procedures described in the Japanese Pharmacopoeia.

The medicinal composition can be provided in a variety of dosage forms, e.g. oral dosage forms such as tablets, capsules (inclusive of soft capsules and microcapsules), powders, granules, and syrups; and non-oral dosage forms such as injections, suppositories, pellets, and drip infusions. These dosage forms can be safely administered either orally or non-orally.

The dosage of the composition for prophylaxis and treatment of the present invention differs depending on the subject, route of administration, clinical condition, etc. For oral administration to an adult patient with cachexia, for instance, the usual unit dose is about 0.1 mg/kg to about 30 mg/kg, preferably about 2 mg/kg to about 20 mg/kg, as the compound of the invention which is an active ingredient, which dose is preferably administered once to 3 times a day.

The composition for prophylaxis and treatment of the present invention can be administered together with other drugs such as chemotherapeutic agents and immunotherapeutic agents to the same subject, either concurrently or at staggered times. The dosage of these drugs can be appropriately selected by referring to the respective recommended clinical dose ranges. The mixing ratio of the composition for prophylaxis and treatment of the present invention and other drugs can be appropriately selected according to the subject, age and body weight of the subject, current clinical status, administration time, dosage form, method of administration, and combination of drugs, among other factors.

The preferred chemotherapeutic agent includes alkylating agents (e.g. cyclophosphamide, ifosfamide), antimetabolites (e.g. methotrexate, 5-fluorouracil), antitumor antibiotics (e.g. mitomycin, adriamycin), antitumor plant alkaloids (e.g. vincristine, vindesine, Taxol), cisplastin, carboplatin, and etoposide. Particularly preferred are Flutron and Neo-Flutron, which are 5-fluorouracil derivatives.

The preferred immunotherapeutic agent includes fungal or bacterial cell wall components (e.g. muramyl dipeptide derivatives, picibanil), immunostimulant polysaccharides (e.g. lentinan, schizophyllan, Krestin), recombinant cytokines (e.g. interferons, interleukins (IL)), and colony stimulating factors (e.g. granulocyte colony stimulating factor, erythropoietin). Particularly preferred are IL-1, IL-2, and IL-12.

Furthermore, drugs which are documented as being anticachectic in an animal model or clinically, such as cyclooxygenase inhibitors (e.g. indomethacin) [Cancer Research, 49, 5935–5939, (1989)], progesterone derivatives (e.g. megestrol acetate) [Journal of Clinical Oncology, 12, 213–225, 1994], glucocorticoids (e.g. dexamethasone), metoclopramides, tetrahydrocannabinols (the same literature as above), lipid metabolism improving agents (e.g. eicosapentanoic acid) [British Journal of Cancer, 68, 314–318, 1993], growth hormone, IGF-1, and antibodies to the cachexia-inducing factors TNF-α, LIF, IL-6, and oncostatin M may also be used together with the composition for prophylaxis and treatment of the present invention.

The compound of the present invention can be used in combination with diuretic. In this case, the administration time of the compound of the present invention and diuretic are not limited, and they can be administered to the same subject, either concurrently or at staggered times. The dosage of the diuretic can be appropriately selected by referring to the recommended clinical dose ranges. The mixing ratio of the compound of the present invention and diuretic can be appropriately selected according to the subject, age and body weight of the subject, current clinical status, administration time, dosage form, method of administration, and combination, among other factors. For example, when the subject is man, diuretic is used in a proportion of usually about 0.01 to about 100 weight parts, preferably about 0.1 to about 20 weight parts, relative to one weight part of the compound of the present invention.

The diuretic includes xanthine derivative preparations (e.g. theobromine and sodium salicylate, theobromine and calcium salicylate), thiazide preparations (e.g. ethiazide, cyclopenthiazide, trichlormethiazide, hydrochlorothiazide, hydroflumethiazide, benzylhydrochlorothiazide, penflutizide, polythiazide, methyclothiazide), antialdosterone preparations (e.g. spironolactone, triamterene), carbonate dehydratase inhibitors (e.g. acetazolamide) chlorbenzenesulfonamide preparations (e.g. chlorthalidone, mefruside, indapamide), azosemide, isosorbide, ethacrynic acid, piretanide, bumetanide, and furosemide.

Among the compound of the present invention, especially a compound which has a bivalent aliphatic hydrocarbon group having 1 to 7 carbon atoms for A in the formula (I) or a salt thereof, has an activity to prevent and treat atherosclerosis, and an activity to regulate appetite and food intake in disorders associated with under-eating, such as anorexia nervosa, and disorders associated with over-eating, such as obesity and anorexia bulimia. Therefore, such a compound or a salt thereof can be used, as such or by providing in a pharmaceutic dosage form in the same manner as described above, as an agent for prophylaxis and treatment of atherosclerosis, or medicine for the regulation of appetite and food intake.

The subject, dosage form, and dosage of the agent for prophylaxis and treatment and the medicine are analogous to those in the case of the above-described composition for prophylaxis and treatment of the present invention.

Among the compound of the present invention, a compound or a salt thereof which has a bivalent aliphatic hydrocarbon group having 1 to 7 carbon atoms for A in the formula (I), has an activity to treat impaired glucose torelance, namely an activity to reduce fasting insulin levels, improve insulin sensitivity, and return glucose torelance to the normal range. Based on such an activity, said compound or a salt thereof can treat impaired glucose torelance in order to prevent or delay the onset of noninsulin-dependent diabetes melitus. Such a compound or a salt thereof can be used, as such or by providing in a pharmaceutic dosage form in the same manner as described above, as a treating agent of impaired glucose torelance.

The subject, dosage form, and dosage of the treating agent are analogous to those in the case of the above-described composition for prophylaxis and treatment of the present invention.

BEST MODE FOR CARRYING OUT THE INVENTION

The following examples and test examples are intended to describe the present invention in further detail and should by no means be construed as defining the scope of the invention.

EXAMPLE 1

Production of Capsules

| | |
|---|---|
| 1) Compound (2) | 100 mg |
| 2) Microcrystalline cellulose | 30 mg |
| 3) Lactose | 37 mg |
| 4) Magnesium stearate | 3 mg |
| Total: | 170 mg |

The above components 1), 2), 3) and 4) were mixed and filled in a gelatin capsule.

EXAMPLE2

Production of Soft Capsules

| | |
|---|---|
| 1) Compound (2) | 50 mg |
| 2) Corn oil | 100 mg |
| Total: | 150 mg |

The components 1) and 2) were mixed and filled in a soft capsule in a conventional manner.

EXAMPLE 3

Production of Tablets

| | |
|---|---|
| 1) Compound (2) | 100 mg |
| 2) Lactose | 34 mg |
| 3) Corn starch | 10.6 mg |
| 4) Corn starch (paste) | 5 mg |
| 5) Magnesium stearate | 0.4 mg |
| 6) Carboxymethylcellulose calcium | 20 mg |
| Total: | 170 mg |

The above components 1) to 6) were mixed and compressed with a tableting machine in a conventional manner.

TEST EXAMPLE 1

Antilipolytic Activity

In accordance with the method of Green et al. [Endocrinology, 134, 2581–2588 (1994)], the antilipolytic activity of the compound of the present invention was evaluated by quantitating the glycerol released from fat cells in rat epididymis adipose tissue.

Thus, the rat epididymis adipose tissue was isolated, cut into pieces with a pair of scissors, and digested into fat cells by agitating in collagenase-containing phosphate buffer for 1 hour. To a culture solution containing fat cells was added 10 ng/ml of IL-1$\beta$ (manufactured by Pharmingen, PM-19101V). Then, in treatment groups, solutions of compound (2) in N,N-dimethylformamide at graded concentrations were respectively added. After 24 hours, the supernatant was recovered and the glycerol therein was quantitated with an assay kit (manufactured by Sigma, 337-A). The amount of released glycerol in each group treated with compound (2) relative to that in the control group was determined to find the inhibition rate and the 50% inhibition concentration $IC_{50}$ of the compound was calculated. The antilipolytic concentration $IC_{50}$ value of compound (2) was 4 nM.

TEST EXAMPLE 2

Weight Loss Inhibitory Activity in Tumor-Bearing Mice

Using the mouse colon cancer cell line Colon 26 (Tanaka et al., Cancer Research, 50, 4528–4532 (1990)), which is a system known to be high in the reproducibility of cancer cachectic symptoms, the inhibitory effect of the compound of the present invention on lipolysis and body weight loss was evaluated.

Thus, $1 \times 10^6$ Colon 26 cells were transplanted subdermaly in 4-week-old CDF1 mice. On day 14 after transplantation, the mice were divided into groups according to tumor size. A 5% (w/v) gum arabic suspension containing compound (2) was administered orally in a dose of 1.0 mg/kg to one group of mice and, as a control, a 5% (w/v) gum arabic suspension was similarly administered to another group, once daily for 7 days in each case. An additional group of mice was not transplanted with Colon 26 cells (normal group). On days 14, 18 and 21 after transplantation, the mice were weighed. On day 22 after transplantation, each mouse was autopsied and the epididymis adipose tissue was isolated and weighed. Changes in mouse body weight and adipose tissue weight are shown in Table 1 and Table 2, respectively.

TABLE 1

Changes in body weight (g) of tumor-bearing mice

| | 14th Day after transplantation | 18th Day after transplantation | 21st Day after transplantation |
|---|---|---|---|
| Normal group | 28.3 | 29.4 | 29.4 |
| Control group | 25.4 | 23.3 | 21.3 |
| Medicated group | 26.3 | 26.3 | 25.6 |

TABLE 2

Adipose tissue weights (mg) of tumor-bearing mice

| | 22nd Day after transplantation |
|---|---|
| Normal group | 769 |
| Control group | 74 |
| Medicated group | 271 |

It will be apparent from Tables 1 and 2 that the compound of the present invention suppresses lipolysis and weight loss which are cancer cachectic symptoms due to transplantation of mouse colon cancer cell line Colon 26, indicating that it is useful as a treating agent for cachexia.

COMPARATIVE EXAMPLE

The antilypolytic activity of indomethacin was evaluated by the same method as in Test Example 1. The antilipolytic concentration $IC_{50}$ value of indomethacin was not less than 10 mM.

INDUSTRIAL APPLICABILITY

The composition for prophylaxis and treatment of the present invention is of value as an agent for prophylaxis and treatment of cachexia which develops in chronic diseases such as malignant tumor, tuberculosis, diabetes, blood dyscrasia, endocrine disease, infectious disease, and acquired immunodeficiency syndrome. The composition for prophylaxis and treatment of the present invention is conducive to relief of the systemic syndrome, the cardinal signs of which are progressive loss of body weight (inclusive of weight loss due to lipolysis and weight loss due to myolysis), anemia, edema, and anorexia, in said chronic diseases.

What is claimed is:

1. A method for treating cachexia selected from the group consisting of cancer cachexia, tuberculous cachexia, hemodyscrasia-related cachexia, endocrine disease-associated cachexia, infectious disease-associated cachexia, and acquired immuno-deficiency syndrome-associated cachexia in a mammal in need thereof, which comprises administering to said mammal an effective amount of a compound of the formula:

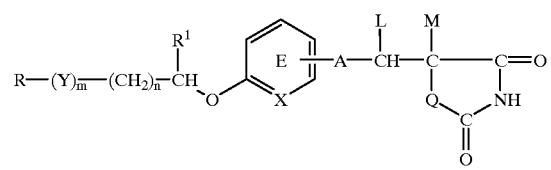

wherein R represents a hydrocarbon group that may be substituted or a heterocyclic group that may be substituted; Y represents a group of the formula —CO—, —CH(OH)—, or —NR$^3$— wherein R$^3$ represents an alkyl group that may be substituted; m is 0 or 1; n is 0, 1 or 2; X represents CH or N; A represents a bond or a bivalent aliphatic hydrocarbon group having 1 to 7 carbon atoms; Q represents oxygen or sulfur; R$^1$ represents hydrogen or an alkyl group; ring E may have further 1 to 4 substituents, which may form a ring in combination with R$^1$; L and M respectively represent hydrogen or may be combined with each other to form a bond; provided that R does not represent dihydrobenzopyranyl when m and n are 0, X represents CH, A represents a bond, Q represents sulfur, R$^1$, L and M respectively represent hydrogen, and ring E does not have further substituents; or a salt thereof.

2. The method according to claim 1, wherein the heterocyclic group represented by R is a 5- to 7-membered heterocyclic group containing 1 to 4 hetero-atoms selected from oxygen, sulfur, and nitrogen in addition to carbon as ring members or a condensed ring group.

3. The method according to claim 1, wherein R represents a heterocyclic group that may be substituted.

4. The method according to claim 3, wherein the heterocyclic group is pyridyl, oxazolyl, or thiazolyl.

5. The method according to claim 1, wherein the partial structural formula:

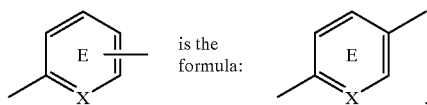

6. The method according to claim 1, wherein n is 0 or 1.

7. The medicinal composition according to claim 1, wherein X represents CH.

8. The method according to claim 1, wherein A represents a bond or a bivalent aliphatic hydrocarbon group having 1 to 4 carbon atoms.

9. The method according to claim 1, wherein $R^1$ represents hydrogen.

10. The method according to claim 1, wherein L and M respectively represent hydrogen.

11. The method according to claim 1, wherein the compound is 5-[4-[2-(5-ethyl-2-pyridyl)ethoxy]benzyl]-2,4-thiazolidinedione, 5-[4-[2-hydroxy-2-(5-methyl-2-phenyl-4-oxazolyl)ethoxy]benzyl-2,4-thiazolidinedione, 5-[3-[3-fluoro-4-(5-methyl-2-phenyl-4-oxazolylmethoxy)phenyl]propyl]-2,4-oxazolidinedione, 5-[5-[3-methoxy-4-(5-methyl-2-phenyl-4-oxazolylmethoxy)phenyl]pentyl=9 -2,4-oxazolidinedione, or (R)-(+)-5-[3-[4-[2-(2-furyl)-5-methyl-4-oxazolylmethoxy]-3-methoxyphenyl]propyl]-2,4-oxazolidinedione.

\* \* \* \* \*

UNITED STATES PATENT AND TRADEMARK OFFICE
CERTIFICATE OF CORRECTION

PATENT NO. : 6,110,948
DATED : August 29, 2000
INVENTOR(S) : Yu Momose et al.

It is certified that error appears in the above-identified patent and that said Letters Patent is hereby corrected as shown below:

Claim 7,
Line 1, change "medicinal composition" to -- method --.

Claim 11,
Line 7, change "pentyl=9" to -- pentyl] --.

Signed and Sealed this

Twenty-fifth Day of December, 2001

Attest:

JAMES E. ROGAN
Attesting Officer   Director of the United States Patent and Trademark Office